(12) United States Patent
Ogasawara et al.

(10) Patent No.: US 9,708,579 B2
(45) Date of Patent: *Jul. 18, 2017

(54) LACTIC ACID BACTERIA FERMENTED SUBSTANCE AND FERMENTED MILK FOOD PRODUCT CONTAINING THE SAME

(75) Inventors: Nobuhiro Ogasawara, Minato-ku (JP); Mayumi Ishii, Minato-ku (JP); Masaki Yoshikawa, Minato-ku (JP); Tatsuyuki Kudo, Minato-ku (JP); Ryoichi Akahoshi, Minato-ku (JP); Akihisa Matsui, Minato-ku (JP); Susumu Mizusawa, Minato-ku (JP); Haruyuki Kimizuka, Chuo-ku (JP); Takao Suzuki, Chuo-ku (JP)

(73) Assignee: KABUSHIKI KAISHA YAKULT HONSHA, Tokyo (JP)

( * ) Notice: Subject to any disclaimer, the term of this patent is extended or adjusted under 35 U.S.C. 154(b) by 198 days.

This patent is subject to a terminal disclaimer.

(21) Appl. No.: 11/915,678

(22) PCT Filed: May 22, 2006

(86) PCT No.: PCT/JP2006/310123
§ 371 (c)(1),
(2), (4) Date: Nov. 27, 2007

(87) PCT Pub. No.: WO2006/126476
PCT Pub. Date: Nov. 30, 2006

(65) Prior Publication Data
US 2008/0292751 A1    Nov. 27, 2008

(30) Foreign Application Priority Data

May 27, 2005  (JP) ................. 2005-155582
May 27, 2005  (JP) ................. 2005-155583
Aug. 12, 2005  (JP) ................. 2005-234747

(51) Int. Cl.
*A23C 9/12*        (2006.01)
*C12N 1/20*        (2006.01)
*A23L 7/10*        (2016.01)
*A23L 33/105*      (2016.01)
*A23L 33/135*      (2016.01)

(52) U.S. Cl.
CPC ............ *C12N 1/20* (2013.01); *A23L 7/115* (2016.08); *A23L 33/105* (2016.08); *A23L 33/135* (2016.08); *A23Y 2220/00* (2013.01)

(58) Field of Classification Search
CPC .... A23L 1/1016; A23L 1/3002; A23L 1/3014; A23L 33/105; A23L 33/135; A23Y 2220/00; C12N 1/20; A01B 12/006
USPC ............................................. 426/34, 43, 61
See application file for complete search history.

(56) References Cited

U.S. PATENT DOCUMENTS 3,677,897 A *  7/1972  Jeffreys ............... 435/252.4
7,115,291 B1 * 10/2006 Kuma et al. ............. 426/43

FOREIGN PATENT DOCUMENTS

| CN | 1377231 A | 10/2002 | |
|---|---|---|---|
| JP | 63 192367 | 8/1988 | |
| JP | 2667421 | 8/1989 | |
| JP | 2 42962 | 2/1990 | |
| JP | 2 142497 | 5/1990 | |
| JP | 2 242667 | 9/1990 | |
| JP | 4 248971 | 9/1992 | |
| JP | 4 248972 | 9/1992 | |
| JP | 5 15366 | 1/1993 | |
| JP | 3223326 | 10/1993 | |
| JP | 6 125771 | 5/1994 | |
| JP | 7 23777 | 1/1995 | |
| JP | 7 51057 | 2/1995 | |
| JP | 2673333 | 4/1995 | |
| JP | 7 170933 | 7/1995 | |
| JP | 9 163977 | 6/1997 | |
| JP | 11 266824 | 10/1999 | |
| JP | 11 266860 | 10/1999 | |
| JP | 11-279069 A * | 12/1999 | ............ A61K 35/78 |
| JP | 2001 190251 | 7/2001 | |
| JP | 2001 190252 | 7/2001 | |
| JP | 2001 190272 | 7/2001 | |
| JP | 2001 238593 | 9/2001 | |

(Continued)

OTHER PUBLICATIONS

Klein, G., et al., Tasonomy and physiology of Probiotic Lactic acid bacteria, Int. J. Food Micro. 41(1998) 103-125.*
Koh, G.Y., Preparation of the Chinese Sweet Leaf Tea Extract and its anti-obesity effect in Rodents, Thesis for Degree of Master of Science, Louisiana State University. Dec. 2009.*
Yun, Jong-Sun et al., "Fermentative Production of DL-Lactic Acid From Amylase-Treated Rice and Wheat Brans Hydrolyzate by a Novel Lactic Acid Bacterium, *Lactobacillus* sp.", Biotechnology Letters, vol. 26, No. 20, p. 1613, 2004.
Oishi, Kazuo et al.,"Development of New Fermented Tea-Drink Using Microorganisms", Shizuoka-Ken Kogyo Gijutsu Senta Kenkyu Hokoku, No. 33, p. 101, 1988.

(Continued)

*Primary Examiner* — Hamid R Badr
(74) *Attorney, Agent, or Firm* — Oblon, McClelland, Maier & Neustadt, L.L.P.

(57) ABSTRACT

An object of the invention is to provide a lactic acid bacteria fermentation product, which has been obtained by culturing lactic acid bacteria on a medium containing an extract of at least one food material selected from the group consisting of rice bran, persimmon leaves, perilla, *Houttuynia cordata* Thunb, *Eucommia ulmoides* Oliv., turmeric, clove, cinnamon and *Rubus suavissimus* S. Lee (Rosaceae). By adding and mixing the extract used for the preparation of the fermentation product to a medium, it is possible to increase simply the viable cell count of lactic acid bacteria, without affecting the flavor of the product. It is possible, by using the extract, to obtain a lactic acid bacteria fermentation product which contains many viable lactic acid bacteria with their activities highly maintained, and further to provide beverages or foods using the product.

13 Claims, No Drawings

(56) References Cited

FOREIGN PATENT DOCUMENTS

| | | |
|---|---|---|
| JP | 2001 352940 | 12/2001 |
| JP | 2002 65199 | 3/2002 |
| JP | 2002-330725 | 11/2002 |
| JP | 2003 88343 | 3/2003 |
| JP | 2003-250528 | 9/2003 |
| JP | 2003 265151 | 9/2003 |
| JP | 2003 289797 | 10/2003 |
| JP | 2004-215529 | 8/2004 |
| JP | 2004-222652 | 8/2004 |
| JP | 2004 345986 | 12/2004 |
| JP | 2005 58132 | 3/2005 |
| JP | 2005 58133 | 3/2005 |
| JP | 2006 28047 | 2/2006 |
| JP | 2006 61091 | 3/2006 |
| KR | 10-0151489 | 8/1995 |
| WO | 01/102331 | 2/2001 |

OTHER PUBLICATIONS

Kobayashi, Toshiaki, "Nyusankin O Riyo Sita Cha no Shinhakko Inryo", Cha, vol. 42, No. 2, p. 16, 1989.

Ouattara, Blaise et al., "Antibacterial Activity of Selected Fatty Acids and Essential Oils Against Six Meat Spoilage Organisms", International Journal of Food Microbiology, vol. 37, p. 155, 1997.

Partanen, Laila et al., "Fats and Fatty Acids as Growth Factors for Lactobacillis Delbrueckii", Systematic and Applied Microbiology, vol. 24, p. 500, 2001.

Kouha Ou, et al., "Preparation of Rice Bran-Based Dietary Fibre Beverage by Lactobacillus Fermentation", China Academic Journal Electronic Publishing House, 2000, vol. 8, pp. 40-41 (with English abstract).

Japanese Office Action dated Jan. 25, 2011 as received in the Japanese corresponding Patent Application No. 2007-517810.

Chinese 3rd Office Action dated Jan. 19, 2011 as received in the corresponding Chinese Application No. 200680018551.4 w/English Translation.

Chinese Office Action issued Apr. 28, 2012, in China Patent Application No. 201110084271.6 (with English translation).

Combined Office Action and Search Report issued Jan. 18, 2013 in Chinese Patent Application No. 201110084271.6 with English language translation.

Jian Liang, "The Research Progress of Sweet Tea", Guangxi Medical Journal, vol. 26, No. 6, Jun. 2004, pp. 845-847.

Office Action as received in the corresponding Korean Patent Application No. 10-2007-7028372 dated Oct. 19, 2012.

Hearing Notice as received in the corresponding Indian Patent Application No. 4899/KOLNP/2007 dated Aug. 8, 2016.

\* cited by examiner

LACTIC ACID BACTERIA FERMENTED SUBSTANCE AND FERMENTED MILK FOOD PRODUCT CONTAINING THE SAME

TECHNICAL FIELD

The present invention relates to lactic acid bacteria fermentation products, and more specifically to lactic acid bacteria fermentation products, which contain viable lactic acid bacteria at high concentration, and also to fermented milk products which contain such lactic acid bacteria fermentation products.

BACKGROUND ART

Culture of lactic acid bacteria is carried out in various manners; most widely by using animal milk in the production of lactic acid bacteria preparations, and also in production of fermented milk, lactic acid bacteria beverages, cheese, etc. However, generally, lactic acid bacteria have different auxotrophy depending on the species, and in general do not sufficiently grow in a medium consisting of only animal milk. Therefore, even with a strain having relatively good proliferability among lactic acid bacteria, culture should be continued for as many as several days to obtain a fermentation product such as fermented milk or lactic acid bacteria beverage, of sufficient acidity upon its production.

Such long-time culture of lactic acid bacteria, however, causes reduction in the viable cell count, and therefore, is not necessarily considered to be a preferred culturing method for the production of lactic acid bacteria beverages, fermented milk, or the like all of which place importance on the viable cell count in expectation of various physiological effects.

In producing various beverages or foods each of which places importance on the flavor of a lactic acid bacteria fermentation product, on the other hand, strains to be used cannot be selected solely from the viewpoint of their proliferativeness. Lactic acid bacteria of poor proliferativeness may be used in some instance for the availability of fermentation products with good flavor.

In the culture of lactic acid bacteria, it is, therefore, common practice to add various growth-promoting substances beforehand to a medium for the purpose of improving the efficiency of the culture. Examples of growth-promoting substance, which are generally considered to be effective, include chlorella extract, iron salts, vitamins, proteolytes including amino acids or peptides, and yeast extract.

Further, as other techniques intended to promote the growth of lactic acid bacteria, there have been recently, reported a method making use of an aqueous extract of sake lees and/or an aqueous extract of sake lees which has been treated with a protease (Patent Document 1), a method making use of an extract from leaves of a plant of *Coffea arabica* (Patent Document 2), a method making use of papaya flesh parts including their skins (Patent Document 3), a method making use of an extract from algal bodies of marine microalgae (Patent Document 4), a method making use of one or more vegetables or the like selected from the group consisting of brocolli, cauliflower, kale, sheperd's purse, radish, tower mustard, celery-leaved buttercup, white celery mustards Japanese bittercress, yellow rocket, watercress, leaf mustard, brown mustard, wasabi (green horseradish paste), herbaceous perennial, long Japanese turnip, Japanese pickling turnip, turnip, oilseed rape, cabbage, spinach, komatuna (*Brassica campestris* var. *peruviridis*), celery, parsley, lettuce and apple (Patent Document 5), a method making use of one or more kinds of vegetables or the like selected from the group consisting of dishcloth gourd, cucumber, sweet melon, pumpkin, yam, taro, 'KONJAK', Japanese radish, carrot, tomato, green pepper, okra, Welsh onion, Chinese cabbage, bean sprouts and tangerine orange (Patent Document 6), a method making use of a tea extract (Patent Documents 7 and 8), a method making use of a calcium salt (Patent Document 9) and a method making use of an extract of ginger, tea or green onion (Patent Document 10), etc.

In order to maintain the usefulness or the efficacy of lactic acid bacteria, however, it is necessary not only to promote the growth of the bacteria but also to reduce death of the bacteria and to improve the viability of the bacteria in the fermentation product by the lactic acid bacteria. Generally, a reduction in the viability of lactic acid bacteria becomes pronounced when preparing a low-fat fermented milk food containing lactic acid bacteria fermentation product of skim milk powder or the like, or when lactic acid fermentation has proceeded too much. The reduction in the viability of lactic acid bacteria, therefore, becomes more serious when preparing a low-calorie fermented milk food or a low-pH fermented milk food. Chlorella or the like is known as a material usable to prevent a viability reduction of lactic acid bacteria, and to maintain the cell count of lactic acid bacteria in a fermented milk food.

In the production of a beverage or food such as a lactic acid bacteria fermentation product or a fermented milk food containing the same, however, a conventionally-known substance added for promoting the growth of lactic acid bacteria or a conventionally-known substance added for improving the viability of lactic acid bacteria may affect the flavor itself of the product in many instances and may also cause a rise in product cost, when used in such an amount as bringing about sufficient effects. Furthermore, even if it is possible to maintain a state that a large amount of viable lactic acid bacteria are contained, the lactic acid bacteria can not be maintained active, thereby making it difficult to expect sufficient physiological effects in some instances.

[Patent Document 1] JP-A-05-015366
[Patent Document 2] JP-A-06-125771
[Patent Document 3] JP-A-07-023777
[Patent Document 4] JP-A-07-051057
[Patent Document 5] JP-A-11-266860
[Patent Document 6] JP-A-02-242667
[Patent Document 7] JP-B-2667421
[Patent Document 8] JP-B-3223326
[Patent Document 9] JP-B-2673333
[Patent Document 10] JP-A-2001-190272

DISCLOSURE OF THE INVENTION

Problems to be solved by the Invention

An object of the present invention is, therefore, to find a novel substance, the mere addition and mixing of which to a medium makes it possible not only to easily increase the viable cell count of lactic acid bacteria but also to maintain the viable cell count even after the preparation of a final product without developing problems about the flavor and taste, and to use the substance for the provision of a lactic acid bacteria fermentation product, said fermentation product containing a number of viable lactic acid bacteria, or a beverage or food making use of the fermentation product.

Means for Solving the Problems

To achieve the above-described object, the present inventors have conducted extensive research. As a result, it has been found that without impairing the flavor and taste of a fermentation product to be obtained by lactic acid bacteria, the proliferative activities of the lactic acid bacteria can be easily improved by adding a novel extract of a specific plant to a medium and culturing the lactic acid bacteria there. Further, the present inventors have also found that culture of lactic acid bacteria on a medium, which contains the above-mentioned extract and a specific fatty acid, makes it possible to obtain a lactic acid bacteria fermentation product which contains viable lactic acid bacteria at high concentration without a reduction in their activities. Furthermore, the present inventors have also found that various beverages or foods, such as fermented milk foods, prepared by the above-mentioned methods are free of any problem in their flavor and taste, leading to the completion of the present invention.

In one aspect of the present invention, there is thus provided a lactic acid bacteria fermentation product, which has been obtained by culturing lactic acid bacteria on a medium comprising an extract of at least one food material selected from the group consisting of rice bran, persimmon leaves, perilla, *Houttuynia cordata* Thunb, *Eucommia ulmoides* Oliv., turmeric, clove, cinnamon and *Rubus suavissimus* S. Lee (Rosaceae).

In another aspect of the present invention, there is also provided a lactic acid bacteria fermentation product, which has been obtained by culturing lactic acid bacteria on a medium comprising an extract of at least one food material selected from the group consisting of rice bran, persimmon leaves, perilla, *Houttuynia cordata* Thunb, *Eucommia ulmoides* Oliv., turmeric, clove, cinnamon and *Rubus suavissimus* S. Lee (Rosaceae), and oleic acid or a derivative thereof.

In a further aspect of the present invention, there is also provided a fermented milk food comprising the above-described fermentation product.

In a still further aspect of the present invention, there is also provided a method for producing a lactic acid bacteria fermentation product, comprising culturing lactic acid bacteria on a medium comprising an extract of at least one food material selected from the group consisting of rice bran, persimmon leaves, perilla, *Houttuynia cordata* Thunb, *Eucommia ulmoides* Oliv., turmeric, clove, cinnamon and *Rubus suavissimus* S. Lee (Rosaceae).

In a yet further aspect of the present invention, there is also provided a method for producing a lactic acid bacteria fermentation product, comprising culturing lactic acid bacteria on a medium comprising an extract of at least one food material selected from the group consisting of rice bran, persimmon leaves, perilla, *Houttuynia cordata* Thunb, *Eucommia ulmoides* Oliv., turmeric, clove, cinnamon and *Rubus suavissimus* S. Lee (Rosaceae), and oleic acid or a derivative thereof.

EFFECT OF THE INVENTION

The extract, which is useful in the lactic acid bacteria fermentation product of the present invention and has been derived from at least one food material selected from the group consisting of rice bran, persimmon leaves, perilla, *Houttuynia cordata* Thunb, *Eucommia ulmoides* Oliv., turmeric, clove, cinnamon and *Rubus suavissimus* S. Lee (Rosaceae), has excellent growth-promoting effects or viability-improving effects for the lactic acid bacteria and moreover, has practically no effect on the flavor and the taste. A fermented milk food, which has been obtained by adding and mixing the extract and contains the lactic acid bacteria fermentation product, is therefore excellent for the promotion of health, and has high utility as a beverage or food which does not undergo any much deterioration in the flavor and taste.

In particular, the combined use of the above-described extract with oleic acid or a derivative thereof can reduce the death of bacteria even in a low-fat fermented milk food or low-pH fermented milk food, thereby guaranteeing the viable cell count in the product and their viability.

BEST MODE FOR CARRYING OUT THE INVENTION

The lactic acid bacteria fermentation product of the present invention is obtained by fermenting lactic acid bacteria under conventionally-known culture conditions, except for the use of a medium which contains an extract of at least one food material selected from the group consisting of rice bran, persimmon leaves, perilla, *Houttuynia cordata* Thunb, *Eucommia ulmoides* Oliv., turmeric, clove, cinnamon and *Rubus suavissimus* S. Lee (Rosaceae) (hereinafter, it may be simply called to as "an extract")

Among the food materials which can each be used as a raw material for the above-mentioned extract, rice bran is a mixture of perocarps, aleurone layers and germs of kernels (brown rice) available from *Oryza sativa* without the chaff of paddy. This rice bran is known to have effects such as immunity enhancement, fatty liver prevention and the like.

Persimmon leaves include leaves of the plant of *Diospyros Kaki* Thunb, *Diospyros lotus* L., or *Diopyros lotus* L. var. *glabra* Makino. In the present invention, *Diospyros Kaki* Thunb are particularly preferred among the plants of the genus *Diospyros* because the leaves are known to have effects such as suppressing sneezing, nasal congestion, runny nose and the like.

Perilla includes *Perilla frustescens* (L.) Britton var. *acuta* Kudo, *Perilla frustescens* (L.) Britton var. *acuta* Kudo forma *viridis* Makino, *Perilla frutescens* (L.) Britton var. *crispa* (Thunb) Decne. In the present invention, *Perilla frustescens* (L.) Britton var. *acuta* Kudo is particularly preferred. To obtain an extract from perilla, leaves, branches and seeds can be used, with the use of leaves being particularly preferred. Perilla is known to have effects such as antiallergic effects, hypoglycemic effects and skin rejuvenation.

*Houttuynia cordata* Thunb. is a plant belonging to *Houttuynia cordata*. To obtain an extract from *Houttuynia cordata* Thunb., aerial grass parts and branch parts can be used, with the use of grass parts being particularly preferred. *Houttuynia cordata* Thunb. is known to have muscosal inflammation suppressing effects.

*Eucommia ulmoides* Oliv. is a plant belonging to *Eucommia ulmoides*. To obtain an extract from *Eucommia ulmoides* Oliv., leaves and branches can be used, with the use of leaves being particularly preferred. *Eucommia ulmoides* Oliv. is known to have effects such as blood pressure control, stress relief and prevention of lifestyle related diseases.

Turmeric is the rootstock of *Curcuma longa* L. or *Curcuma aromatica* Salisb. In the present invention, *Curcuma longa* L. is particularly preferred among plants belonging to *Curcuma*. *Curcuma longa* L. is known to have effects such as hepatic function improving effects, hangover preventing effects, gastric antisecretory effects and gastrointestinal dysfunction improving effects.

Clove is the bud of *Syzygium aromaticum* (L.) Merr. et Perry or *Eugenia caryophyllata* Thunb. Clove is known to have preservation effects, uterine contraction activities, dental pain reduction effects, and the like.

Cinnamon is the bark of *Cinnamomum zeylanicum* Nees or *Cinnamomum cassia* Blume. *Cinnamomum zeylanicum* Nees is particularly preferred among these cinnamomum plants. Cinnamon is known to have effects such as antibacterial activities, body-warming effects, antipyretic effects, digestive system activation effects, amelioration effects for various cold symptoms, indigestion relief, diarrhea relief and nausea relief.

*Rubus sauvissimus* S. Lee (Rosaceae) is a plant belonging to *Rubus*. To obtain an extract from *Rubus sauvissimus* S. Lee (Rosaceae), its leaves and stem can be used, with the use of its leaves being particularly preferred. *Rubus sauvissimus* S. Lee (Rosaceae) is attracting attention in recent years for its anti-inflammatory activities and antiallergic effects.

To obtain an extract from one or more of the above-described food materials, it is only necessary to extract with a solvent the food material or materials either as they are or after optionally applying processings such as washing, peeling, drying and/or crushing. Such extracts may be used either singly or in combination. A mixed extract may also be used, which is obtained by mixing a plurality of food materials and extracting them. Among these extracts, preferred are an extract from persimmon leaves and an extract from *Rubus sauvissimus* S. Lee (Rosaceae).

Solvents usable in the extraction include water and organic solvents such as lower alcohols having 1 to 5 carbon atoms, e.g., ethanol, ethyl acetate, glycerol and propylene glycol. Two or more of these solvents may be used together as a mixed solvent. Among these solvents, water and aqueous solvents such as water-lower alcohols are particularly preferred.

No particular limitation is imposed on the extraction method of an extract from one or more of the above-mentioned food materials with the above-mentioned solvent, but acid extraction is preferred as it can efficiently extract from the food material or materials components which enhance the proliferative activities of lactic acid bacteria and can also bring about excellent growth-promoting effects even when the extract is added in a small amount. Acid extraction can preferably be performed under an acidic condition of pH 4.0 or lower, especially pH 3.0 to 4.0. No particular limitation is imposed on acid ingredient adapted to regulate the pH of the solvent in this acid extraction, and any ingredient can be used insofar as it is acidic. Among such acid ingredients, preferred are organic acids such as citric acid, malic acid, tartaric acid, succinic acid, lactic acid and acetic acid.

Furthermore, extraction conditions for the extract with the use of the above-mentioned solvent are not particularly limited, and the extraction processing can be carried out, for example, by treatment for 30 to 60 minutes preferably at 60° C. to 120° C., more preferably at 80° C. to 100° C.

The extract obtained as described above may be used as a solution as obtained immediately after the extraction, or as a concentrated extract obtained by purification and concentration of the obtained extract by means of ultrafiltration, centrifugation or the like, or as a powdery extract obtained by further drying the concentrated extract by means of spray drying, freeze drying or the like.

Upon adding the above-mentioned extract to a medium where lactic acid bacteria can grow, its amount may preferably be determined after an experimental verification since the resulting growth-promoting effects may differ depending on the strains to be cultured, the composition of the medium and the application of the cultured product. In general, however, the extract may be added in an amount preferably of about 0.01 to 10% by weight (hereinafter, simply referred to as "%"), more preferably of about 0.01% to 5% as calculated in terms of an extract having 10 degrees Brix (sugar content).

These extracts may be added in an amount greater than 10% or more. However, the growth-promoting effects may not be brought about as much as proportional to the amount added. On the contrary, such an excessively large amount of the extract may affect the flavor and taste of the beverage or food containing the resulting medium. It is, therefore, not preferred to add the extract in such an excessively large amount. An amount of such an extract smaller than 0.01%, on the other hand, may not bring about the growth-promoting effects sufficiently and, therefore, is not preferred.

In the present invention, it is possible to obtain synergic growth-promoting effects and viability-improving effects for lactic acid bacteria by adding oleic acid or a derivative thereof (hereinafter, simply referred to as "theoleic acid") to the medium containing the extract. No particular limitation is imposed on the oleic acid to be added together with the extract to the medium, and illustrative are free oleic acid, inorganic salts of oleic acid, and sugar esters, glycerides, sorbitan esters and propylene glycol esters, which are used commonly as emulsifiers, and contain oleic acid as their fatty acid moietier. It is also possible to use food materials which contain a large amount of the oleic acid. It is, however, to be noted that among those containing the oleic acid in their structures, those having such a form as lysolecithin or the like may not be able to obtain the effects of maintaining the bacterial cell count and activities in the lactic acid bacteria fermentation product of the invention.

Preferred specific examples of the oleic acid include oleate salts such as sodium oleate and potassium oleate, and oleate esters such as glyceryl oleate, polyglyceryl oleate acid ester and sucrose oleate. Among the above-described oleate esters, glyceryl oleate or polyglyceryl oleate is preferred for its high effects of increasing the cell count and improving viability upon completion of the culture. From the stand point in physical properties such as solubility in media, sucrose oleate is preferred. These oleic acids may be used singly or in combination.

The oleic acid can preferably be added to a medium in such an amount that its final concentration in the product becomes 5 to 50 ppm, preferably 5 to 25 ppm in terms of oleic acid. An amount of the oleic acid smaller than 5 ppm may not be able to sufficiently exhibit the synergic effects of activating growth and suppressing death of bacteria in the product when used in combination with the extract. An amount of the oleic acid greater than 50 ppm, on the other hand, may develop a problem in cost and may inhibit the proliferability of bacteria, and therefore, is not preferred.

In the present invention, the timing of addition of the extract and the oleic acid to a medium can preferably be, but not limited thereto, before the fermentation by lactic acid bacteria. They can also be added during the fermentation by lactic acid bacteria, or after the completion of the fermentation by lactic acid bacteria. They can be added in several portions. It is particularly preferred to add the extract and the oleic acids before the fermentation by lactic acid bacteria, because the cell count and the viability of the bacteria upon completion of the culture can be maintained at high levels.

Media to which the extract and the oleic acid are to be added include animal milk media composed of fresh milks such as cow milk, goat milk, horse milk and sheep milk or dairy products such as skim milk powder, whole milk powder and fresh cream, and various synthetic media. These media may be those containing ingredients which are used in ordinary media for lactic acid bacteria. Such ingredients include, for examples, vitamins such as vitamin A, vitamin Bs, vitamin C and vitamin E, various peptides and amino acids, and salts such as calcium salts and magnesium salts.

In the present invention, no particular limitation is imposed on the lactic acid bacteria to be used for culture insofar as it is a microorganism commonly used in the production of foods. Illustrative are bacteria of the genus *Lactobacillus* such as *Lactobacillus casei, Lactobacillus acidophilus, Lactobacillus cremoris, Lactobacillus helveticus, Lactobacillus salivarius, Lactobacillus gasseri, Lactobacillus fermentum, Lactobacillus yoghurti, Lactobacillus delbrueckii* subsp. *bulgaricus, Lactobacillus delbrueckii* subsp. *delbrueckii* and *Lactobacillus johnsonii*, bacteria of the genus *Streptococcus* such as *Streptococcus thermophilus*, bacteria of genus *Lactococcus* such as *Lactococcus lactis* subsp. *lactis, Lactococcus lactis* subsp. *cremoris, Lactococcus plantarum* and *Lactococcus raffinolactis*, bacteria of the genus *Enterococcus* such as *Enterococcus faecalis* and *Enterococcus faecium*. Among these lactic acid bacteria, it is preferred to use one or more species selected from the group consisting of the bacteria of the genus *Lactobacillus*, the bacteria of the genus *Streptococcus* and the bacteria of the genus *Lactococcus*. It is to be noted that the term "lactic acid bacteria" as used herein means facultative anaerobic bacteria, and does not include the bacteria of the genus *Bifidobacteria*, which are anaerobic bacteria.

The above-mentioned lactic acid bacteria also include those which do not grow sufficiently with media composed of animal milks, and the extract for use in the present invention brings about particularly remarkable effects in the culture of such bacteria. Specifically, excellent growth-promoting effects can be obtained when the extract is added to media upon culturing lactic acid bacteria such as *Lactobacillus casei, Lactobacillus acidophilus, Lactobacillus cremoris, Lactobacillus helveticus, Lactobacillus gasseri, Lactobacillus delbrueckii* subsp. *bulgaricus, Streptococcus thermophilus* and *Lactococcus lactis* subsp. *lactis*.

No particular limitations are imposed on the culture conditions for lactic acid bacteria in order to obtain the lactic acid bacteria fermentation product of the present invention. For example, however, culture may be conducted at about 30 to 40° C. for 1 to 7 days. As further conditions for such culture, a method suited for lactic acid bacteria to be cultured may be selected from a standing, stirring, shaking, aeration or like method.

The lactic acid bacteria fermentation product obtained as described above contains viable lactic acid bacteria at high concentration without a reduction in their proliferativeness. This product can be mixed with other auxiliary materials, the addition of which to foods is generally approved, to produce fermented milk foods.

The term "fermented milk foods" includes fermented milks, dairy products, beverages such as lactic acid bacteria beverages, hard yogurt, soft yogurt, plain yogurt and further, kefir, cheese, etc., which are defined by the Ministerial Ordinance concerning Compositional Standards, etc. for Milk and Milk Products. Fermented milk foods of the present invention, therefore, include various beverages and foods making use of various lactic acid bacteria, for example, fermented milks, lactic acid bacteria beverages, kefir, cheese and the like, which can be of the plain type, flavored type, fruit type, sweetened type, soft type, drink type, solid (hard) type or frozen type.

These fermented milk foods are obtained by adding, to the above-described lactic acid bacteria fermentation product, a sweetener such as starch syrup and various other food materials, for example, optional ingredients such as various carbohydrates, thickeners, emulsifiers and various vitamins, as needed. Specific examples of these food materials include carbohydrates such as sucrose, glucose, fructose, paratinose, trehalose, lactose, xylose and maltose; glycoalcohols such as sorbitol, xylitol, erythritol, lactitol, palatinate, reduced starch syrup and reduced maltose syrup; sweeteners of high sweetness intensity such as aspartame, thaumatin, sucralose, acesulfame K and stevia; various thickeners (stabilizers) such as agar, gelatin, carrageenan, guar gum, xanthane gum, pectin, locust bean gum, gellan gum, carboxymethylcellulose, soybean polysaccharides and propylene glycol alginate; emulsifiers such as sucrose fatty acid esters, glycerine fatty acid esters, polyglycerine fatty acid esters, sorbitan fatty acid esters and lecithin; milk fats such as cream; butter and sour cream; sours seasonings such as citric acid, lactic acid, acetic acid, malic acid, tartaric acid and gluconic acid; various vitamins such as vitamin A, vitamin Bs, vitamin C and vitamin E; minerals such as calcium, magnesium, zinc, iron and manganese; and flavorings such as yogurt, berry, orange, Chinese quince, perilla, citrus, apple, mint, grape, apricot, pear, custard cream, peach, melon, banana, tropical, herb, black tea and coffee.

The fermented milk food obtained as described-above has a high utility as a beverage or food, which has good flavor and taste, is excellent in health promotion, and does not undergo much deteriorations in flavor and taste. In addition, the lactic acid bacteria fermentation product of the present invention is excellent in growth-promoting effects and viability-improving effects for lactic acid bacteria owing to the extract added to the culture, and therefore, has and maintains a sufficient lactic acid bacteria cell count. When oleic acid or the like is incorporated in the medium in addition to the extract, synergic effects are recognized with respect to the growth-promoting effects and viability-improving effects of lactic acid bacteria.

Although the mechanism of action of the extract on the growth-promoting effects and viability-improving effects for lactic acid bacteria in the present invention has not been elucidated yet, it is presumed that the extract contains abundant minerals, and these minerals contribute to the growth promotion and viability improvement of lactic acid bacteria. It is also presumed that, when the extract is combined with oleic acids or the like, synergic effects of the minerals and oleic acid or the like achieve the growth promotion and viability improvement of lactic acid bacteria.

EXAMPLES

The present invention will hereinafter be described in further detail based on Examples. It should, however, be borne in mind that the present invention is by no means limited to the following examples.

Example 1

<Extract Preparation 1>

Turmeric (the rootstock of *Curcuma lonqa* L.) the aerial grass part of *Houttuynia cordata* Thunb., leaves of *Eucommmia ulmoides* Oliv., persimmon leaves (leaves of *Diospyros kaki* Thunb.), leaves of *Perilla frutescens* (L.) Britton var. *acuta* Kudo, clove (the bud of *Syzygium aramaticum* (L.) Merr. et Perry) and cinnamon (the bark of *Cinnamomum zeylanium* Nees) were each separately subjected to processings such as peeling and crushing, and then extracted for 60 minutes with hot water of 90° C. (in an amount 10 times as much as the weight of the corresponding raw material) to prepare extracts of turmeric, *Houttuynia cordata* Thunb.,

*Eucommia ulmoides* Oliv., persimmon leaves, perilla, clove and cinnamon, respectively. The extracts were each separately concentrated to 10 degrees Brix in an evaporator.

Example 2

<Comparison in the Proliferability of Lactic Acid Bacteria>

As a basal medium, 12% skim milk powder, was furnished. The extracts of turmeric, *Houttuynia cordata* Thunb., *Eucommia ulmoides* Oliv., persimmon leaves, perilla, clove, and cinnamon, which had been prepared and adjusted to 10 degrees Brix in Example 1, were added at 1% to aliquots of the basal medium, respectively, followed by sterilization to prepare sterilized media. To each of those media, a starter of *Lactobacillus casei* YIT9029 was inoculated at 1%, and the bacteria strain was then cultured at 37° C. for 48 hours. Employed as a comparative medium was one prepared by adding "MEAST" (trademark for brewery beer yeast autolysate; product of Asahi Food and Healthcare Co., Ltd.) at 0.15% to the basal medium and then sterilizing the medium. The amount of "MEAST" so added is the upper limit of a range in which its adverse effects on the flavor and taste of the culture is acceptable.

The proliferabilities of the lactic acid bacteria in the respective cultures were then compared relying upon the acidities of the cultures (titration values of 0.1 N caustic soda when portions (9 g) of the respective cultures were taken and an organic acid in the respective cultured portions 0.1 N caustic soda until pH 8.5 was reached; unit: mL) as indicies. The results are shown below in Table 1.

TABLE 1

| Basal medium | MEAST | Turmeric extract | *Houttuynia cordata* Thunb. extract | *Eucommia ulmoides* Oliv. extract | Persimmon leaf extract | *Perilla* extract | Clove extract | Cinnamon extract |
|---|---|---|---|---|---|---|---|---|
| Acidity |||||||||
| 8.2 | 10.1 | 11.1 | 10.9 | 11.0 | 11.3 | 10.7 | 10.9 | 10.7 |

As is clear from Table 1, it has been confirmed that the acidity becomes higher in a medium with an extract of turmeric, *Houttuynia cordata* Thunb., *Eucommia ulmoides* Oliv., persimmon leaves, perilla, clove or cinnamon added therein, than in a medium without the addition of any extract or a medium with "MEAST" added therein. This indicates that the growth of lactic acid bacteria can be promoted by these extracts.

Example 3

<Verification of Effects of Acid Extraction Extract on Proliferability of Lactic Acid Bacteria>

Under similar conditions as in the extract preparation in Example 1 except for the use of water and aqueous solutions, the pHs of which had been adjusted to 3.0, 4.0 and 5.0, respectively, with citric acid instead of hot water, persimmon leaves were treated. To aliquots of a 15% skim milk powder medium (with 3% glucose contained therein), said aliquots containing the thus-obtained extracts added therein at 1%, respectively, the starter of *Lactobacillus casei* YIT9029 was inoculated at 1%. The bacteria strain was then cultured at 35° C. for 5 days. The acidities of the resultant cultures were measured in a similar manner as in Example 2. The results are shown in Table 2.

TABLE 2

| Test Strain | Hot water | pH 3.0 | pH. 4.0 | pH 5.0 |
|---|---|---|---|---|
| *Lactobacillus casei* YIT9029 | 23.1 | 24.4 | 24.5 | 23.5 |

As shown in Table 2, it has been confirmed that the proliferability for lactic acid bacteria when tends to become remarkable with an extract obtained by adjusting the pH of an extraction solvent to 5.0 or less.

Example 4

<Extract Preparation 2>

Turmeric (the rootstock of *Curcuma longa* L.), the aerial grass part of *Houttuynia cordata* Thunb., leaves of *Eucommia ulmoides* Oliv., persimmon leaves (leaves of *Diospyros kaki* Thunb.), leaves of *Perilla frutescens* (L.) Britton var. *acuta* Kudo, clove (the bud of *Syzygium aramaticum* (L.) Merr. et Perry) and cinnamon (the bark of *Cinnamomum zeylanium* Nees), were each separately subjected to processings such as peeling and crushing, and then extracted under similar conditions as in Example 1 except for the use of water and an aqueous solution, the pH of which had been adjusted to pH 4.0 with citric acid, (in amounts 10 times as much as the weight of the corresponding raw material) to prepare extracts of turmeric, *Houttuynia cordata* Thunb., *Eucommia ulmoides* Oliv., persimmon leaves, perilla, clove and cinnamon, respectively. They were each separately concentrated to 10 degrees Brix, in an evaporator.

Example 5

<Verification of Effects of Extract on Proliferability of Lactic Acid Bacteria>

As a basal medium, 16% skim milk powder was furnished. The extract of turmeric, *Houttuynia cordata* Thunb., *Eucommia ulmoides* Oliv., persimmon leaves, perilla, clove and cinnamon by 1%, which had been adjusted to 10 degrees Brix in Example 4, were added at 1% to aliquots of the basal medium to prepare media, respectively. Into each of those media, the starters of various lactic acid bacteria strains were inoculated at 0.1%, and those bacteria strains were cultured at 37° C. for 48 hours. In the above culture were used *Lactobacillus casei*, *Lactobacillus acidophilus*, *Lactobacillus cremoris*, *Lactobacillus helveticus*, *Lactobacillus gasseri*, *Lactobacillus delbrueckii* subsp. *bulgaricus*, *Streptococcus thermophilus* and *Lactococcus lactis* subsp. *lactis*.

The acidities of the resultant cultures were measured in a similar manner as in Example 2 to compare the proliferabilities of the various lactic acid bacteria. The results are shown in Table 3.

TABLE 3

| Test strain | Basal medium | Turmeric extract | Houttuynia cordata Thunb. extract | Eucommia ulmoides Oliv. extract | Persimmon leaf extract | Perilla extract | Clove extract | Cinnamon extract |
|---|---|---|---|---|---|---|---|---|
| | | | | Acidity | | | | |
| Lactobacillus casei YIT9029 | 8.1 | 13.5 | 13.1 | 13.0 | 14.0 | 12.2 | 14.1 | 13.2 |
| Lactobacillus acidophilus YIT0070 | 9.0 | 11.4 | 10.7 | 11.1 | 11.7 | 11.4 | 10.0 | 10.4 |
| Lactobacillus cremoris YIT2002 | 1.4 | 6.7 | 6.1 | 6.4 | 7.1 | 5.8 | 6.2 | 6.1 |
| Lactobacillus helveticus YIT0100 | 17.2 | 17.8 | 17.2 | 17.5 | 17.7 | 17.4 | 17.5 | 17.6 |
| Lactobacillus gasseri YIT0192 | 2.8 | 9.1 | 9.5 | 9.8 | 10.0 | 8.1 | 8.1 | 7.2 |
| Lactobacillus delbrueckii subsp. bulgaricus YIT0098 | 14.9 | 16.1 | 15.8 | 16.4 | 16.2 | 15.4 | 16.7 | 16.1 |
| Streptococcus thermophilus YIT2001 | 7.6 | 8.9 | 8.5 | 8.9 | 8.7 | 7.9 | 8.4 | 8.1 |
| Lactococcus lactis subsp. lactis YIT2013 | 6.2 | 7.2 | 6.8 | 6.9 | 7.0 | 6.2 | 6.4 | 6.5 |

As is clear from Table 3, the effects of these extracts on the proliferability of various lactic acid bacteria have been confirmed with substantially all the strains, although they vary depending on the species of the strains. Remarkable effects have been confirmed particularly with the extracts of turmeric, Houttuynia cordata Thunb., Eucommia ulmoides Oliv. and persimmon leaves. Further, the proliferative effects have been confirmed to have a tendency of giving excellent effects to strains which are poor in proliferation on the basal medium. This suggests even when lactic acid bacteria hard to grow in an animal medium is used, the use of these extracts make it possible to easily obtain a culture of a large cell count.

Example 6

<Preparation of Lactic Acid Bacteria Beverage>

A 15% skim milk powder medium (with 3% of glucose contained therein) was furnished as a basal medium. The various extracts prepared in Example 4 were added at 0.1% to aliquots of the basal medium to provide test media, respectively. After sterilizing those media under heat, the starter of Lactobacillus casei YIT9029 was inoculated at 0.5% to the respective media, and the bacteria strain was cultured at 35° C. for 5 days to obtain respective cultures. Each culture was homogenized at 15 MPa, and to 20 parts by weight of that culture, 80 parts by weight of a 15% sugar solution, which had been sterilized at 100° C. for 5 minutes, was added, and a yogurt flavoring (product of Yakult Material Co., Ltd.) was further added at 0.1% to prepare a dairy product. A taste test was conducted by five well-experienced assessors on each of the dairy products obtained as descried above. No difference was confirmed between any of the lactic acid bacteria beverages and the control product which contained the culture obtained with the use of the basal medium.

In addition, the various extracts were assessed to give no flavor and/or taste-related effects to the basal medium and to match very well. It has, therefore, been also confirmed that their use in cultures for beverages or foods such as lactic acid bacteria beverages does not lead to deteriorations in their flavors or tastes.

Example 7

<Effects of Added Amount of Persimmon Leaf Extract on Flavor and Taste and Proliferative Effects>

(1) Preparation of Persimmon Leaf Extracts

Using water and a solution, the pH of which has been adjusted to 4.0 with citric acid, in amounts of 10 times as much as persimmon leaves, persimmon leaf extracts were prepared under similar conditions as in Example 1. Those extracts were each separately concentrated to 10 degrees Brix in an evaporator.

(2) Determination of an Amount to be Added

To aliquots of a 15% skim milk powder medium (with 3% of glucose contained therein) the persimmon leaf extracts prepared above in (1) was added at concentrations in a range of 0.01 to 10%, respectively, followed by sterilization at 100° C. for 60 minutes to prepare media for culturing lactic acid bacteria. To those media, the starter of Lactobacillus casei YIT9029 was inoculated at 1%, and the bacteria strain was cultured at 35° C. until the acidities (titration values of 0.1 N sodium hydroxide required for the neutralization of 9 g portions of the respective samples) became 24. The cell count of the lactic acid bacteria in each of the cultures was determined by BCP medium. Each culture was homogenized at 15 MPa, and to 20 parts by weight of the homogenized culture, 80 parts by weight of a 15% sugar solution, which had been sterilized at 100° C. for 5 minutes, was added, and a yogurt flavoring (product of Yakult Material Co., Ltd.) was further added at 0.1% to prepare a dairy product. With respect to such dairy products a flavor and taste assessment was conducted by five trained organoleptic assessors based on the following standards. The results are shown in Table 4.

| <Assessment standards> | |
|---|---|
| (Ranking) | (Description) |
| A: | Very good |
| B: | Good |
| C: | Average |
| D: | Poor |
| E: | Very poor |

TABLE 4

| | Added amount of persimmon leaf extract (%) | Culture time (hrs) | Viable cell count of lactic acid bacteria (/mL) | Flavor and taste assessment |
|---|---|---|---|---|
| Not added | 0 | 192 | $1.9 \times 10^9$ | A |
| Water extraction | 0.01 | 147 | $2.7 \times 10^9$ | A |
| | 0.1 | 130 | $3.2 \times 10^9$ | A |
| | 1 | 121 | $5.5 \times 10^9$ | B |
| | 5 | 116 | $5.3 \times 10^9$ | B |
| | 10 | 116 | $5.2 \times 10^9$ | D |
| Acid extraction (pH 4.0) | 0.01 | 128 | $3.5 \times 10^9$ | A |
| | 0.1 | 120 | $5.4 \times 10^9$ | A |
| | 1 | 117 | $5.7 \times 10^9$ | B |
| | 5 | 117 | $5.9 \times 10^9$ | B |
| | 10 | 115 | $5.5 \times 10^9$ | D |

It has been confirmed from Table 4 that the addition of an extract of persimmon leaves at 0.1% or so is effective for the promotion of culture by lactic acid bacteria, and moreover, can increase the viable cell count of lactic acid bacteria. It has also been ascertained that the addition of an extract of persimmon leaves even as much as 10% to a medium can not bring about any additional excellent effects in proportion to the amounts added, but on the contrary, the flavor and taste derived from the extract tend to affect the flavor and taste of the product. It has also been confirmed that the growth-promoting effects of the extract are exhibited more remarkably with one obtained by acid extraction than with one obtained by water extraction.

Example 8

<Extract Preparation 3>

Rice bran (a mixture of pericarps, aleurone layers and germs of kernels (brown rice) available from *Oryza sativa* without the chaff of paddy), turmeric (the rootstock of *Curcuma longa* L.), aerial grass part of *Houttuynia cordata* Thunb., layers of *Eucommia ulmoides* Oliv., persimmon leaves (leaves of *Diospyros kaki* Thunb.), leaves of *Perilla frutescens* (L.) Britton var. *acuta* Kudo, clove (the bud of *Syzygium aramaticum* (L.) Merr. et Perry) and cinnamon (the bark of *Cinnamomum zeylanium* Nees) were each separately subjected to processings such as peeling and crushing, and then extracted for 60 minutes with hot water of 80° C. (in an amount 10 times as much as the weight of the corresponding raw material) to prepare extracts of turmeric, *Houttuynia cordata* Thunb., *Eucommia ulmoides* Oliv., persimmon leaves, perilla, clove and cinnamon, respectively. The extracts were each separately concentrated to 10 degrees Brix in an evaporator.

Example 9

<Determination of Lactic Acid Bacteria Cell Count Upon Completion of Culture (1)>

To aliquots of a 15% skim milk powder medium (with 3% of glucose contained therein) as a basal medium, the extracts of rice bran, persimmon leaves, perilla, *Houttuynia cordata* Thunb., *Eucommia ulmoides* Thunb., turmeric, clove and cinnamon, which were prepared and adjusted to 10 degrees Brix in Example 8, were added at 1%, respectively, followed by sterilization at 100° C. for 60 minutes to prepare sterilized media. To those sterilized media, the starter of *Lactobacillus casei* YIT9029 was inoculated at 1%, and the bacteria strain was cultured at 37° C. until the pHs of the respective media reached 3.7. The viable cell counts were similarly determined upon completion of the culture. In addition, a medium with sodium oleate added in place of the above-described extract to give a concentration of 25 ppm in terms of oleic acid and another medium with both of the above-described extract and sodium oleate added were also prepared. The viable cell counts were similarly determined upon completion of the culture. It is to be noted that determination of each viable cell count was performed by counting colonies formed after incubating the corresponding sample, which had been suitably diluted in a physiological solution, at 37° C. for 3 days on BCP medium. The results are shown in Table 5.

TABLE 5

| | Additive | Cell count of lactic acid bacteria (cfu/mL) | | Additive(s) | Cell count of lactic acid bacteria (cfu/mL) |
|---|---|---|---|---|---|
| Comparative Product 1 | Not added | $1.9 \times 10^9$ | Comparative Product 2 | Sodium oleate | $2.1 \times 10^9$ |
| Invention Product 1 | Rice bran extract | $4.7 \times 10^9$ | Invention Product 2 | Rice bran extract, sodium oleate | $7.1 \times 10^9$ |
| Invention Product 3 | Persimmon leaf extract | $5.2 \times 10^9$ | Invention Product 4 | Persimmon leaf extract, sodium oleate | $7.8 \times 10^9$ |
| Invention Product 5 | *Perilla* extract | $3.6 \times 10^9$ | Invention Product 6 | Perilla extract, sodium oleate | $6.6 \times 10^9$ |
| Invention Product 7 | *Houttuynia cordata* Thunb. extract | $4.2 \times 10^9$ | Invention Product 8 | *Houttuynia cordata* Thunb. extract, sodium oleate | $7.0 \times 10^9$ |
| Invention Product 9 | *Eucommia ulmoides* Oliv. extract | $4.3 \times 10^9$ | Invention Product 10 | *Eucommia ulmoides* Oliv. extract, sodium oleate | $7.4 \times 10^9$ |
| Invention Product 11 | Turmeric extract | $4.2 \times 10^9$ | Invention Product 12 | Turmeric extract, sodium oleate | $6.8 \times 10^9$ |
| Invention Product 13 | Clove extract | $4.5 \times 10^9$ | Invention Product 14 | Clove extract, sodium oleate | $6.9 \times 10^9$ |
| Invention Product 15 | Cinnamon extract | $4.4 \times 10^9$ | Example Product 16 | Cinnamon extract, sodium oleate | $6.4 \times 10^9$ |

It has been indicated from Table 5 that the combined use of anyone of extracts of rice bran, persimmon leaves, perilla, *Houttuynia cordata* Thunb., *Eucommia ulmoides* Thunb., turmeric, clove and cinnamon with sodium oleate can synergically increase the cell count of lactic acid bacteria upon completion of the culture as compared with the single use of the same extract or sodium oleate.

Example 10

<Determination of Viable Cell Count of Lactic Acid Bacteria in Dairy Product (1)>

The cultures prepared in Example 9 (Comparative Products 1 and 2 and Invention Products 3 and 4) were each separately homogenized at 15 MPa. To aliquots (20 parts by weight) of those homogenized cultures, 80 parts by weight of a 15% sugar solution which had been sterilized at 100° C. for 5 minutes were added, followed by the further addition of a yogurt flavoring at 0.1% to prepare dairy products. Those dairy products were filled in containers, and the viable cell counts were determined in a similar manner as in Example 9 immediately after the production of the dairy products and after their storage at 10° C. for 14 days. The results are shown in Table 6.

TABLE 6

| | Additive(s) | | Cell count of lactic acid bacteria (cfu/mL) | |
| --- | --- | --- | --- | --- |
| | | | Immediately after production | After storage at 10° C. for 14 days |
| Comparative Product 3 | Not added | | $4.2 \times 10^8$ | $1.1 \times 10^8$ |
| Comparative Product 4 | Sodium oleate | 25 ppm | $9.0 \times 10^8$ | $4.4 \times 10^8$ |
| Invention Product 17 | Persimmon leaf extract | 1% by weight | $1.0 \times 10^9$ | $3.8 \times 10^8$ |
| Invention Product 18 | Persimmon leaf extract Sodium oleate | 1% by weight 25 ppm | $1.8 \times 10^9$ | $1.1 \times 10^9$ |

It has been indicated from Table 6 that a dairy product obtained by using, as a raw material, a culture prepared by using an extract of persimmon leaves and sodium oleate in combination is excellent in its effect to suppress changes in the cell count of lactic acid bacteria in the product during storage as compared with a dairy product available from the use of a culture which contains none of them (not added) or contains only one of them.

Example 11

<Determination of Viable Cell Count of Lactic Acid Bacteria Upon Completion of Culture (2)>

*Lactobacillus casei* YIT9029 was cultured under similar conditions as in Example 9 except that to aliquots of the basal medium prepared in Example 9, various oleate-based emulsifiers were added respectively, each in combination with 1% of the extract of persimmon leaves prepared in Example 8, such that the emulsifiers amounted to 25 ppm in terms of the content of oleic acid. The viable cell counts of the bacteria in the resulting cultures were determined according to the method of Example 9. The results are shown in Table 7.

TABLE 7

| | Additive(s) | Cell count of Lactic acid bacteria (cfu/mL) |
| --- | --- | --- |
| Invention Product 19 | Persimmon leaf extract | $2.3 \times 10^9$ |
| Invention Product 20 | Persimmon leaf extract, sodium oleate | $7.1 \times 10^9$ |
| Invention Product 21 | Persimmon leaf extract, glyceryl oleate | $7.3 \times 10^9$ |
| Invention Product 22 | Persimmon leaf extract, pentaglyceryl trioleate | $3.9 \times 10^9$ |
| Invention Product 23 | Persimmon leaf extract, hexaglyceryl monooleate | $6.9 \times 10^9$ |
| Invention Product 24 | Persimmon leaf extract, decaglyceryl decaoleate | $4.2 \times 10^9$ |
| Invention Product 25 | Persimmon leaf extract, sucrose oleate | $7.0 \times 10^9$ |
| Invention Product 26 | Persimmon leaf extract, glyceryl oleate | $3.2 \times 10^9$ |

It has been indicated from Table 7 that the use of the oleic acid as derived from any one of the emulsifiers can provide the resulting culture with a higher cell count of lactic acid bacteria owing to the use of the extract of persimmon leaves in combination.

The use of glyceryl oleate, hexaglyceryl monooleate or sucrose oleate among these emulsifiers can bring about remarkable effects.

Example 12

<Determination of Viable Cell Count of Lactic Acid Bacteria Upon Completion of Culture (3)>

Under similar conditions as in the extract preparation in Example 8 except for the use of water and aqueous solutions, the pHs of which has been adjusted to pH to 3.0, 4.0 and 5.0, respectively with citric acid instead of hot water, rice bran, persimmon leaves, *Eucommia ulmoides* Thunb., turmeric and clove were each treated to prepare their extracts of 10 degrees Brix. To aliquots of a 15% skim milk powder medium with the thus-prepared extracts added at 0.1%, respectively, sodium oleate was added at 25 ppm in terms of the content of oleic acid, and further, the starter of *Lactobacillus casei* YIT9029 was inoculated at 1%. The bacteria strain was then cultured at 37° C. until the pH reached 3.7. The viable cell counts of lactic acid bacteria in the resultant cultures were determined according to the method of Example 9. The results are shown in Table 8.

TABLE 8

| | Additives | Extraction pH | Cell count of lactic acid bacteria (cfu/mL) |
|---|---|---|---|
| Invention Product 27 | Rice bran extract, | 5.0 | $7.1 \times 10^9$ |
| Invention Product 28 | sodium oleate | 4.0 | $9.0 \times 10^9$ |
| Invention Product 29 | | 3.0 | $9.4 \times 10^9$ |
| Invention Product 30 | Persimmon leaf | 5.0 | $8.5 \times 10^9$ |
| Invention Product 31 | extract, | 4.0 | $8.8 \times 10^9$ |
| Invention Product 32 | sodium oleate | 3.0 | $9.6 \times 10^9$ |
| Invention Product 33 | *Eucommia ulmoides* | 5.0 | $7.0 \times 10^9$ |
| Invention Product 34 | Oliv. extract, | 4.0 | $8.4 \times 10^9$ |
| Invention Product 35 | sodium oleate | 3.0 | $9.1 \times 10^9$ |
| Invention Product 36 | Turmeric extract, | 5.0 | $7.4 \times 10^9$ |
| Invention Product 37 | sodium oleate | 4.0 | $8.5 \times 10^9$ |
| Invention Product 38 | | 3.0 | $8.4 \times 10^9$ |
| Invention Product 39 | Clove extract, | 5.0 | $7.0 \times 10^9$ |
| Invention Product 40 | sodium oleate | 4.0 | $8.5 \times 10^9$ |
| Invention Product 41 | | 3.0 | $8.4 \times 10^9$ |

It has been indicated from Table 8 that an extract obtained by acid extraction tends to provide a higher cell count upon completion of culture as the pH of the solvent used in the extraction becomes lower. This effect is pronouncedly observed especially with various extracts obtained at pH 5.0 or lower, more preferably, pH 4.0 or lower.

Example 13

<Determination of Viable Cell Count of Lactic Acid Bacteria Upon Completion of Culture (4)>

Using a citric acid solution of pH 4.0, an extract of persimmon leaves of 10 degrees Brix was prepared under similar conditions as in Example 8. To 10% skim milk powder, the extract was added at 1% and further, sodium oleate was also added at 25 ppm in terms of oleic acid. The resultant mixture was sterilized to prepare a sterilized medium. To aliquots of that sterilized medium, starters of various lactic acid bacteria were inoculated at 0.1%, respectively and the bacteria strains were cultured at 37° C. for 24 hours. As the lactic acid bacteria, were used *Lactobacillus bulgaricus* YIT0098, *Lactobacillus acidophilus* YIT0071 and *Lactobacillus casei* YIT9029. In addition, those lactic acid bacteria were cultured in similar manner as described above in a 10% skim milk powder medium for the sake of comparison. The lactic acid bacteria cell counts in the resultant cultures were determined in a similar manner as in Example 9. The results are shown in Table 9.

TABLE 9

| | | Cell count of lactic acid bacteria (cfu/mL) | |
|---|---|---|---|
| | Additives | Medium with no addition | Medium with addition |
| *Lactobacillus bulgaricus* YIT0098 | Persimmon leaf extract, | $3.3 \times 10^8$ | $6.8 \times 10^8$ |
| *Lactobacillus acidophilus* YIT0071 | sodium oleate | $3.5 \times 10^6$ | $2.4 \times 10^7$ |
| *Lactobacillus casei* YIT9029 | | $7.7 \times 10^8$ | $5.0 \times 10^9$ |

It has been indicated from Table 9 that the effect of increasing the lactic acid bacteria cell count, which is available from the combined use of an acid-extracted persimmon leaf extract and sodium oleate, can be recognized for all lactic acid bacteria although the effect has been confirmed to somewhat differ depending on the species of the lactic acid bacteria.

Example 14

<Determination of Viable Cell Count of Lactic Acid Bacteria Upon Completion of Culture (5)>

Using a citric acid solution of pH 4.0, an extract of persimmon leaves of 10 degrees Brix was prepared under similar conditions as in Example 8. The extract and glyceryl oleate, as oleic acid, were added to aliquots of a 15% skim milk powder medium (with 3% of glucose contained therein) such that their added amounts reached those shown below in Table 10, respectively. The resultant media were sterilized at 100° C. for 60 minutes, to prepare sterilized media. To the respective sterilized media, the starter of *Lactobacillus casei* YIT9029 was inoculated at 1%, and the bacteria strain was cultured at 37° C. until their pHs reached 3.7. In addition, culture was similarly carried out as a control by adding an yeast extract (product of DIFCO), which is generally known as a culture promoter, at 0.2% to the medium. The lactic acid bacteria cell counts in the resultant cultures were determined in a similar manner as in Example 9. The results are shown in Table 10.

TABLE 10

| Added amount of persimmon leaf extract (%) | Added amount of oleic acid (ppm) | | | |
|---|---|---|---|---|
| | 0 | 5 | 25 | 50 |
| 0 | $2.3 \times 10^9$ | | | |
| 0.01 | | $5.0 \times 10^9$ | $5.1 \times 10^9$ | $5.4 \times 10^9$ |
| 0.1 | | $7.4 \times 10^9$ | $8.0 \times 10^9$ | $7.6 \times 10^9$ |
| 5.0 | | $8.5 \times 10^9$ | $9.0 \times 10^9$ | $9.1 \times 10^9$ |
| 10.0 | | $9.1 \times 10^9$ | $9.5 \times 10^9$ | $9.4 \times 10^9$ |
| Yeast extract (0.2) | $2.7 \times 10^9$ | | | |

It has been confirmed from Table 10 that the effect of increasing the viable cell count be clearly recognized by adding 0.1% or more of the persimmon leaf extract and 5 ppm or more of oleic acid in combination. It has also been indicated that the resulting viable cell count is greater than that available from the addition of an yeast extract.

Example 15

<Determination of Viable Cell Count of Lactic Acid Bacteria in Dairy Product (2)>

Using the cultures prepared in Example 14, dairy product were produced in a similar manner as in Example 10. A flavor and taste assessment was performed by five trained organoleptic assessors on those dairy products on the basis of the following standards. The results are shown in Table 11.

| <Assessment standards> | |
|---|---|
| (Ranking) | (Description) |
| A: | Very good |
| B: | Good |
| C: | Average |
| D: | Poor |
| E: | Very poor |

TABLE 11

| Added amount of persimmon leaf extract (%) | Added amount of oleic acid (ppm) | | | |
|---|---|---|---|---|
| | 0 | 5 | 25 | 50 |
| 0 | B | | | |
| 0.01 | | B | B | B |
| 0.1 | | B | B | B |
| 5.0 | | B | B | B |
| 10.0 | | C | C | C |
| Yeast extract (0.2) | | D | | |

It has been indicated from Table 11 that when addition of the extract of persimmon leaves at 16% to the medium, i.e., at 2% per dairy product affects the flavor and taste of the dairy product irrespective of the added amount of oleic acid and therefore, that this added amount can be considered to be the acceptable addition upper limit. It is to be noted that even with the addition amount of the persimmon leaf extract in that amount, the product had a better flavor and taste than that available from the addition of the yeast extract.

Example 16

<Extract Preparation 4>

Leaves of *Rubus suavissimus* S. Lee (Rosaceae) were subjected to processings such as peeling, crushing and roasting, and then extracted for 60 minutes with hot water of 90° C. (in an amount of 10 times as much as the weight of the leaves of *Rubus suavissimus* S. Lee (Rosaceae)), to prepare an extract of *Rubus suavissimus* S. Lee (Rosaceae). The resultant extract was concentrated to 10 degrees Brix in an evaporator.

Example 17

<Verification of the Effects for Lactic Acid Bacteria (1)>

As a basal mesium, 12% skim milk powder was furnished. The extract of *Rubus suavissimus* S. Lee (Rosaceae), which had been prepared and adjusted to 10 degrees Brix in Example 16, was added at 0.5% to the basal medium followed by sterilization to prepare a sterilized medium. To that sterilized medium, the starter of *Lactobacillus casei* YIT9029 was inoculated at 1%, and the bacteria strain was cultured at 37° C. for 48 hours. Employed as a comparative example was one prepared by adding "MEAST" (trademark for brewery yeast autolysate; product of Asahi Food and Healthcare Co., Ltd.) at 0.15% to the basal medium and then sterilizing the medium. The amount of "MEAST" so added is the upper limit of a range in which its adverse effects on the flavor and taste of the culture is acceptable.

The proliferability of the lactic acid bacteria in which the culture was then compared relying upon the acidity of the culture (titration value of 0.1 N caustic soda when a portion (9 g) of culture was taken and an organic acid in the culture portion was reached; unit: mL as an index). The results are shown in Table 12.

TABLE 12

| | Acidity |
|---|---|
| Basal medium | 8.0 |
| "MEAST" | 10.0 |
| *Rubus suavissimus* S. Lee (*Rosaceae*) extract | 11.7 |

As evident from Table 12, it has been confirmed that the acidity becomes higher in a medium with the *Rubus suavissimus* S. Lee (Rosaceae) extract added therein than in a medium with no addition or with "MEAST" added therein. This indicates that the proliferablity of lactic acid bacteria can be promoted by a *Rubus suavissimus* S. Lee (Rosaceae) extract.

Example 18

<Verification of the Effects for Lactic Acid Bacteria (2)>

Under similar conditions as in the extract preparation method in Example 16 except for the use of aqueous solutions (90° C.), the pHs of which has been adjusted to pH 3.0, 4.0 and 5.0, respectively with citric acid instead of hot water, leaves of *Rubus suavissimus* S. Lee (Rosaceae) were treated to prepare *Rubus suavissimus* S. Lee (Rosaceae) extracts of 10 degrees Brix. To aliquots of a 15% skim milk powder medium (with 3% of glucose contained therein), said aliquots containing the thus-obtained extracts added therein at 1%, respectively the starter of *Lactobacillus casei* YIT9029 was inoculated at 1%. The bacteria strain was cultured at 35° C. for 5 days. The acidities of the resultant cultures were measured in a similar manner as in Example 17. The results are shown in Table 13.

TABLE 13

| Test Strain | Hot water | pH 3.0 | pH 4.0 | pH 5.0 |
|---|---|---|---|---|
| *Lactobacillus casei* YIT9029 | 23.2 | 24.6 | 24.8 | 23.8 |

As shown in Table 13, it has been confirmed that the proliferability for lactic acid bacteria tends to become remarkable with a *Rubus suavissimus* S. Lee (Rosaceae) extract obtained by adjusting the pH of an extraction solvent to 5.0 or lower.

Example 19

<Extract Preparation 5>

Leaves of *Rubus suavissimus* S. Lee (Rosaceae) were subjected to processings such as peeling, crushing and roasting, and then extracted under similar conditions as in Example 16 with an aqueous solution of citric acid adjusted to pH 4.0 (in an amount of 10 times as much as the weight of the leaves of *Rubus suavissimus* S. Lee (Rosaceae)) to prepare an extract of *Rubus suavissimus* S. Lee (Rosaceae). The thus-obtained extract was concentrated to 10 degrees Brix in an evaporator.

Example 20

<Verification of the Effects for Lactic Acid Bacteria (3)>

A 16% skim milk powder was furnished as a basal medium, and to medium, the *Rubus suavissimus* S. Lee (Rosaceae) extract adjusted to 10 degrees Brix in Example 19 at 1% to prepare a medium. To aliquots of that medium, starters of various lactic acid bacteria were inoculated at 0.1%, and the bacteria strains were cultured at 37° C. for 48 hours.

In above culture were used *Lactobacillus casei, Lactobacillus acidophilus, Lactobacillus cremoris, Lactobacillus helveticus, Lactobacillus gasseri, Lactobacillus delbrueckii* subsp. *bulgaricus, Streptococcus thermophilus* and *Lactococcus lactis* subsp. *lactis*.

The acidities of the resultant cultures were measured in a similar manner as in Example 17 to compare the proliferability of the various lactic acid bacteria. The results are shown in Table 14.

TABLE 14

| Test Strain | Basal medium | Rubus suavissimus S. Lee (Rosaceae) Extract |
|---|---|---|
| Lactobacillus casei YIT9029 | 8.7 | 14.5 |
| Lactobacillus acidophilus YIT0070 | 9.2 | 11.4 |
| Lactobacillus cremoris YIT2002 | 1.2 | 6.5 |
| Lactobacillus helveticus YIT0100 | 17.0 | 17.0 |
| Lactobacillus gasseri YIT0192 | 2.2 | 11.0 |
| Lactobacillus delbrueckii subsp. bulgaricus YIT0098 | 14.5 | 16.5 |
| Streptococcus thermophilus YIT2001 | 7.0 | 8.2 |
| Lactococcus lactis subsp. lactis YIT2013 | 6.4 | 6.8 |

As is clear from Table 14, the effects of the *Rubus suavissimus* S. Lee (Rosaceae) extract on the proliferability of the various lactic acid bacteria have been confirmed with substantially all the strains, although they vary depending on the species of the strains. Further, these proliferative effects have been confirmed to have tendency of giving excellent effects to strains which are not very good in proliferation on the basal medium. This suggests that even when lactic acid bacteria hard to grow in an animal medium is used, the use of a *Rubus suavissimus* S. Lee (Rosaceae) extract makes it possible to easily obtain a fermentation product with a large number of bacteria cell count.

Example 21

<Investigation on the Amount of *Rubus suavissimus* S. Lee (Rosaceae) Extract to be Added>

(1) Preparation of *Rubus suavissimus* S. Lee (Rosaceae) Extract

Using an aqueous solution of citric acid the pH of which had been adjusted to pH 4.0, in an amount as much as leaves of *Rubus suavissimus* S. Lee (Rosaceae), a *Rubus suavissimus* S. Lee (Rosaceae) extract was prepared under similar conditions as in Example 16. The extract was then concentrated to 10 degrees Brix in an evaporator.

(2) Determination of an Amount to be Added

To aliquots of a 15% skim milk powder medium (with 3% of glucose contained therein), *Rubus suavissimus* S. Lee (Rosaceae) extract of 10 degrees Brix, which was prepared above in (1) was added at concentrations in a range of 0.01 to 10%, respectively, followed by sterilization at 100° C. for 60 minutes to prepare a medium for culturing lactic acid bacteria. To those media, the starter of *Lactobacillus casei* YIT9029 was inoculated at 1%, and the bacteria strain was cultured at 35° C. until the acidities (titration values of 0.1 N sodium hydroxide required for neutralization of 9 g portions of respective samples) became 24. The cell count of the lactic acid bacteria in each of the cultures was determined by BCP medium. The culture was homogenized at 15 MPa, and to 20 parts by weight of the homogenized culture, 80 parts by weight of a 15% sugar solution, which had been sterilized at 100° C. for 5 minutes at 100° C. were added, and a yogurt flavoring (product of Yakult Material Co., Ltd.) was further added at 0.1% to prepare a dairy product. With respect to such dairy products, a flavor and taste assessment was performed by five trained organoleptic assessors on the base of the following standards. The results are shown in Table 15.

<Assessment standards>

| (Ranking) | (Description) |
|---|---|
| A: | Very good |
| B: | Good |
| C: | Average |
| D: | Poor |
| E: | Very poor |

TABLE 15

| | Added amount of Rubus suavissimus S. Lee (Rosaceae) extract (%) | Culture time (hrs) | Viable cell count of lactic acid bacteria (cfu/mL) | Flavor and taste assessment |
|---|---|---|---|---|
| Not added | 0 | 184 | $1.2 \times 10^9$ | A |
| Water extraction | 0.01 | 144 | $2.3 \times 10^9$ | A |
| | 0.1 | 123 | $3.0 \times 10^9$ | A |
| | 1 | 120 | $4.2 \times 10^9$ | A |
| | 5 | 118 | $4.5 \times 10^9$ | B |
| | 10 | 116 | $4.8 \times 10^9$ | C |
| Acid extraction (pH 4.0) | 0.01 | 132 | $3.0 \times 10^9$ | A |
| | 0.1 | 121 | $4.2 \times 10^9$ | A |
| | 1 | 118 | $5.1 \times 10^9$ | A |
| | 5 | 115 | $4.9 \times 10^9$ | B |
| | 10 | 115 | $5.3 \times 10^9$ | C |

It has been confirmed from Table 15 that the addition at 0.01% or so of an extract of *Rubus suavissimus* S. Lee (Rosaceae) can bring about proliferative effects for lactic acid bacteria, and moreover, can increase the viable cell count of lactic acid bacteria. It has also been ascertained that the addition of an extract *Rubus suavissimus* S. Lee (Rosaceae) even as much as more than 10% does not bring about extra effect in proportion to the amount so added, but on the contrary, tends to affect the flavor and taste of the product. It has also been confirmed that the effects of the extract are exhibited more remarkably with one obtained by acid extraction, than with one obtained by water extraction.

Example 22

<Verification of the Effects for Lactic Acid Bacteria (4)>

To aliquots of a 15% skim milk powder medium (with 3% of glucose contained therein) as a basal medium, the *Rubus suavissimus* S. Lee (Rosaceae) extracts, which were prepared and adjusted to 10 degrees Brix in Example 16 and Example 19, respectively were added at 1%, respectively, followed by sterilization at 100° C. for 60 minutes to prepare sterilized media. To those media, the starter of *Lactobacillus casei* YIT9029 was inoculated at 1%, and the bacteria strain, which was cultured at 37° C. until the pHs of the respective media reached 3.7. The viable cell counts were determined upon completion of the culture. In addition, a medium with sodium oleate added instead of the above-described extract to give a concentration of 25 ppm in terms of oleic acid and another medium both of the above-described extract and sodium oleate added were also prepared. The viable cell counts were similarly determined upon completion of the culture. It is to be noted that the determination of each viable cell count was performed by counting the colonies formed after incubating the corresponding sample, which has been suitably diluted in a physiological solution, saline solution at 37° C. for 3 days on BCP medium. The results are shown in Table 16.

TABLE 16

| | Additive(s) | Cell count of lactic acid bacteria (cfu/mL) |
|---|---|---|
| Comparative Product 5 | Not added | $1.7 \times 10^9$ |
| Invention Product 42 | *Rubus suavissimus* S. Lee (*Rosaceae*) extract (hot water) | $4.1 \times 10^9$ |
| Invention Product 43 | *Rubus suavissimus* S. Lee (*Rosaceae*) extract (pH 4.0) | $5.4 \times 10^9$ |
| Comparative Product 6 | Sodium oleate | $2.5 \times 10^9$ |
| Invention Product 44 | *Rubus suavissimus* S. Lee (*Rosaceae*) extract (hot water), sodium oleate | $5.5 \times 10^9$ |
| Invention Product 45 | *Rubus suavissimus* S. Lee (*Rosaceae*) extract (pH 4.0), sodium oleate | $6.5 \times 10^9$ |

It has been confirmed from Table 16 that the combined use of any one of the *Rubus suavissimus* S. Lee (*Rosaceae*) extracts with sodium oleate can synergically increase the cell count of lactic acid bacteria as compared with the single use of the corresponding *Rubus suavissimus* S. Lee (*Rosaceae*) extract.

Example 23

<Verification of the Effects for Lactic Acid Bacteria (5)>

The lactic acid bacteria fermentation products prepared in Example 22 (Invention Products 42, 43, 44 and 45) were each separately homogenized at 15 MPa, and to 20 parts by weight aliquots of the homogenized products, 80 parts by weight aliquots of a 15% sugar solution, which had been sterilized at 100° C. for 5 minutes were added, and a yogurt flavoring was further added at 0.1% to prepare dairy products. Those dairy products were filled in containers, respectively and the viable cell counts of the lactic acid bacteria in the respective dairy products were determined in a similar manner as in Example 22 immediately after their preparation and after their storage at 10° C. for 14 days. The results are shown in Table 17.

TABLE 17

| | Additive(s) | | Cell count of lactic acid bacteria (cfu/mL) | |
|---|---|---|---|---|
| | | | Immediately after preparation | After storage at 10° C. for 14 days |
| Comparative Product 7 | Not added | | $3.4 \times 10^8$ | $9.7 \times 10^7$ |
| Invention Product 46 | *Rubus suavissimus* S. Lee (*Rosaceae*) extract (hot water) | 1% by weight | $8.2 \times 10^8$ | $4.4 \times 10^8$ |
| Invention Product 47 | *Rubus suavissimus* S. Lee (*Rosaceae*) extract (hot water) Sodium oleate | 1% by weight 25 ppm | $1.3 \times 10^9$ | $7.4 \times 10^8$ |
| Invention Product 48 | *Rubus suavissimus* S. Lee (*Rosaceae*) extract (pH 4.0) | 1% by weight | $1.0 \times 10^9$ | $5.4 \times 10^8$ |
| Invention Product 49 | *Rubus suavissimus* S. Lee (*Rosaceae*) extract (pH 4.0) Sodium oleate | 1% by weight 25 ppm | $1.4 \times 10^9$ | $8.4 \times 10^8$ |

It has been indicated from Table 17 that a dairy product obtained by using, as a raw material, a lactic acid bacteria fermentation product, which has been prepared by using a *Rubus suavissimus* S. Lee (*Rosaceae*) extract singly, or a *Rubus suavissimus* S. Lee (*Rosaceae*) extract and sodium oleate in combination, is excellent in the effect of suppressing changes in the cell count of lactic acid bacteria in the product during storage as compared with a dairy product obtained by using a lactic acid bacteria fermentation product prepared with none of them. Further, the use of a *Rubus suavissimus* S. Lee (*Rosaceae*) extract in combination with sodium oleate can synergically bring about the effects as opposed to the single use of the *Rubus suavissimus* S. Lee (*Rosaceae*) extract.

Example 24

<Verification of the Effects for Lactic Acid Bacteria (6)>

Using an aqueous citric acid solution of pH 4.0, an extract of *Rubus suavissimus* S. Lee (*Rosaceae*) of 10 degrees Brix was prepared under similar conditions as in Example 16. To 10% skim milk powder, that extract was added at 1% and further, sodium oleate was also added at 25 ppm in term of oleic acid. The resultant mixture was sterilized to prepare a sterilized medium. To aliquots of that medium, starters of various lactic acid bacteria were inoculated at 0.1%, respectively and the bacteria strains were cultured at 37° C. for 24 hours. As the lactic acid bacteria, were used *Lactobacillus delbrueckii* subsp. *bulgaricus*, *Lactobacillus acidophilys* and *Lactobacillus casei*. As comparative examples, those lactic acid bacteria were also cultured in a similar manner as described above by using 10% skim milk powder as a medium. The cell counts of lactic acid bacteria in the resultant cultures were determined in a similar manner as in Example 22. The results are shown in Table 18.

TABLE 18

| Test Strain | Cell count of lactic acid bacteria (cfu/mL) | |
|---|---|---|
| | Medium with no addition | Medium with addition |
| Lactobacillus bulgaricus YIT0098 | $3.0 \times 10^8$ | $6.5 \times 10^8$ |
| Lactobacillus acidophilus YIT0071 | $3.5 \times 10^8$ | $6.4 \times 10^8$ |
| Lactobacillus casei YIT9029 | $8.2 \times 10^8$ | $2.4 \times 10^9$ |

It has been indicated from Table 18 that the effects of a *Rubus suavissimus* S. Lee (*Rosaceae*) extract and oleic acid can be recognized for all lactic acid bacteria, although the effects have been confirmed to somewhat differ depending on the species of the lactic acid bacteria.

Example 25

<Verification of the Effects for Lactic Acid Bacteria (7)>

To aliquots of a 15% skim milk powder medium (with 3% glucose contained therein) as a basal medium, various oleate-based emulsifiers were added respectively, each in combination with 1% of the *Rubus suavissimus* S. Lee (*Rosaceae*) extract prepared and adjusted to 10 degreed Brix in Example 19, such that the emulsifiers amounted to 25 ppm in terms of the content of oleic acid. The resulting mixtures were then sterilized at 100° C. for 60 minutes to prepare sterilized media, respectively. To those media, the starter of *Lactobacillus casei* YIT9029 was inoculated at 1%, and the bacteria strain was cultured at 37° C. until the pHs of the respective media reached 3.7. The viable cell counts were measured in a similar manner as in Example 21. The results are shown in Table 19.

TABLE 19

| | Added material | Cell count of lactic acid bacteria (cfu/mL) |
|---|---|---|
| Invention Product 50 | *Rubus suavissimus* S. Lee (*Rosaceae*) extract | $1.8 \times 10^9$ |
| Invention Product 51 | *Rubus suavissimus* S. Lee (*Rosaceae*) extract, sodium oleate | $6.0 \times 10^9$ |
| Invention Product 52 | *Rubus suavissimus* S. Lee (*Rosaceae*) extract, monoglyceryl oleate | $6.5 \times 10^9$ |
| Invention Product 53 | *Rubus suavissimus* S. Lee (*Rosaceae*) extract, pentaglyceryl trioleate | $4.2 \times 10^9$ |
| Invention Product 54 | *Rubus suavissimus* S. Lee (*Rosaceae*) extract, hexaglyceryl monooleate | $5.0 \times 10^9$ |
| Invention Product 55 | *Rubus suavissimus* S. Lee (*Rosaceae*) extract, decaglycerine decaoleate | $4.2 \times 10^9$ |
| Invention Product 56 | *Rubus suavissimus* S. Lee (*Rosaceae*) extract, sucrose oleate | $6.4 \times 10^9$ |
| Invention Product 57 | *Rubus suavissimus* S. Lee (*Rosaceae*) extract, glyceryl oleate | $3.1 \times 10^9$ |

It has been confirmed that as shown in Table 19, the use of the oleic acid as derived from any one of the emulsifiers can bring about proliferative effects for lactic acid bacteria owing to the use of the extract of *Rubus suavissimus* S. Lee (*Rosaceae*) in combination. The use of sodium oleate monoglyceryl oleate or sucrose oleate among these emulsifiers can bring about remarkable effects.

Example 26

<Verification of the Effects for Lactic Acid Bacteria (8)>

Using an aqueous citric acid solution of pH 4.0, an extract of *Rubus suavissimus* S. Lee (*Rosaceae*) adjusted to 10 degrees Brix was prepared under similar conditions as in Example 16. The extract and glyceryl oleate, as oleic acid, were added to aliquots of 15% skim milk powder medium (with 3% of glucose contained therein) such that their added amount reached those shown below in Table 20, respectively. The resultant media were sterilized at 100° C. for 60 minutes to prepare sterilized media. To the respective sterilized media, the starter of *Lactobacillus casei* YIT9029 was inoculated at 1%, and the bacteria strain was cultured at 37° C. until their pHs reached 3.7. In addition, culture was similarly carried out as a control by adding an yeast extract (product of DIFCO), which is generally known as a culture promoter, at 0.2% to the medium. The lactic acid bacteria cell counts in the resultant cultures were determined in a similar manner as in Example 22. The results are shown in Table 20.

TABLE 20

| Added amount of *Rubus suavissimus* S. Lee (*Rosaceae*) extract (%) | Added amount of oleic acid (ppm) | | | |
|---|---|---|---|---|
| | 0 | 1 | 25 | 50 |
| 0 | $1.8 \times 10^9$ | | | |
| 0.01 | $2.8 \times 10^9$ | $3.5 \times 10^9$ | $4.2 \times 10^9$ | $4.0 \times 10^9$ |
| 0.1 | $4.0 \times 10^9$ | $4.9 \times 10^9$ | $5.9 \times 10^9$ | $6.2 \times 10^9$ |
| 1.0 | $4.9 \times 10^9$ | $6.1 \times 10^9$ | $8.1 \times 10^9$ | $7.8 \times 10^9$ |
| 5.0 | $5.2 \times 10^9$ | $6.3 \times 10^9$ | $8.2 \times 10^9$ | $8.5 \times 10^9$ |
| 10.0 | $5.0 \times 10^9$ | $6.1 \times 10^9$ | $8.4 \times 10^9$ | $8.3 \times 10^9$ |
| Yeast extract (0.2) | $2.3 \times 10^9$ | | | |

As shown in Table 20, proliferative effects for lactic acid bacteria can be recognized by the addition of oleic acid at 0.01 ppm or higher.

Example 27

<Verification of the Effects for Lactic Acid Bacteria (9)>

Using the lactic acid fermentation product prepared in Example 26, dairy products were produced in a similar manner as in Example 21. A flavor and test assessment was performed by five trained organoleptic assessors on those dairy products on the basis of similar assessment standards as in Example 21. The results are shown in Table 21.

TABLE 21

| Added amount of Rubus suavissimus S. Lee (Rosaceae) extract (%) | Added amount of oleic acid (ppm) | | | |
|---|---|---|---|---|
| | 0 | 1 | 25 | 50 |
| 0 | A | | | |
| 0.01 | A | A | A | A |
| 0.1 | A | A | A | A |
| 1.0 | A | A | A | A |
| 5.0 | B | B | B | B |
| 10.0 | C | C | C | C |
| Yeast extract (0.2) | | D | | |

It has been found from Table 21 that similarly to the indication of Table 15, the addition of the *Rubus suavissimus* S. Lee (Rosaceae) extract at 10% to the medium, i.e., at 2% per product affects the flavor and taste of the product irrespective of the added amount of oleic acid. It is to be noted that even with the addition of the *Rubus suavissimus* S. Lee (Rosaceae) extract is that amount, the product had a better flavor and taste than that available from the addition of the yeast extract.

INDUSTRIAL APPLICABILITY

The lactic acid bacteria fermentation product of the present invention has a large amount of viable cell count of lactic acid bacteria. The fermentation product does not undergo much deteriorations in flavor and taste as death of the lactic acid bacteria can be reduced. Accordingly, this lactic acid bacteria fermentation product can be suitably used as a raw material for various fermented dairy foods.

The invention claimed is:

1. A fermented milk food consisting of live *Lactobacillus casei*, an acid extraction extract of *Rubus suavissimus* S. Lee (Rosaceae), and optionally one or more of a milk component, flavor, stabilizer, a sweetener, oleic acid, oleic acid salt, and oleic acid ester;
    wherein said acid extraction extract is prepared by extracting *Rubus suavissimus* S. Lee (Rosaceae) in an aqueous acid solution at pH 4.0 or less;
    wherein said acid extraction extract is included in an amount ranging from 0.01% to 1% by weight of the fermented milk food as calculated in terms of an extract adjusted to 10 degrees Brix (sugar content); and
    wherein said extract is present in an amount sufficient to increase the viability of the *Lactobacillus casei* in the fermented milk food after storage at 10° C. for 14 days compared to the viability of *Lactobacillus casei* in an otherwise identical fermented milk food which does not contain the extract.

2. The fermented milk food of claim 1 that is produced by fermenting a milk medium selected from the group consisting of a cow milk, goat milk, horse milk, and sheep milk; or a combination thereof.

3. The fermented milk food of claim 1 that is produced by fermenting a milk medium containing at least one ingredient selected from the group consisting of skim milk powder, whole milk powder and fresh cream, and synthetic milk media; or a combination thereof.

4. The fermented milk food of claim 1, wherein said acid extraction extract is included in an amount ranging from 0.01% to 0.1% by weight as calculated in terms of an extract adjusted to 10 degrees Brix (sugar content).

5. The fermented milk food of claim 1, wherein at least one of oleic acid, oleic acid salt, or oleic acid ester is present and is in an amount ranging from 5 to 50 ppm.

6. The fermented milk food of claim 1, wherein the oleic acid salt is present, the oleic acid salt is glyceryl oleate, polyglyceryl oleate, or both and is present in an amount ranging from 5 to 50 ppm.

7. The fermented milk food of claim 1, wherein the oleic acid ester is present, the oleic acid ester is sucrose oleate ester and is present in an amount ranging from 5 to 50 ppm.

8. A method for making the fermented milk food of claim 1 consisting of:
    fermenting a milk medium at least one of the group consisting of a cow milk, goat milk, horse milk, sheep milk, skim milk powder, whole milk powder, fresh cream, synthetic milk media, and a combination thereof with live *Lactobacillus casei* in the presence of an acid extraction extract of *Rubus suavissimus* S. Lee (Rosaceae), and optionally one or more of a milk component, flavor, stabilizer, a sweetener, oleic acid, oleic acid salt, and oleic acid ester;
    wherein said acid extraction extract is prepared by extracting *Rubus suavissimus* S. Lee (Rosaceae) in an aqueous acid solution at pH 4.0 or less;
    wherein said acid extraction extract is included in an amount ranging from 0.01% to 1% by weight as calculated in terms of an extract adjusted to 10 degrees Brix (sugar content).

9. The method of claim 8, wherein 0.01% to 0.1% of the acid extraction extract of *Rubus suavissimus* S. Lee (Rosaceae) is present in the milk medium.

10. The method of claim 8, wherein the at least one of oleic acid, oleic acid salt, or oleic acid ester is present in the milk medium and is in an amount ranging from 5 to 50 ppm.

11. The method of claim 8, wherein *Lactobacillus casei* proliferation during fermentation is higher than in an otherwise identical method wherein the medium does not contain the acid extraction extract of *Rubus suavissimus* S. Lee (Rosaceae).

12. The method of claim 8, wherein viability of *Lactobacillus casei* in the fermented milk food is higher than that in a fermented milk food produced by an otherwise identical method wherein the medium does not contain the acid extraction extract of *Rubus suavissimus* S. Lee (Rosaceae); wherein *Lactobacillus casei* viability is determined after storage of the fermented milk food at 10° C. for 14 days.

13. A fermented milk food consisting of live *Lactobacillus casei*, an acid extraction extract of *Rubus suavissimus* S. Lee (Rosaceae), and optionally one or more of a milk component, flavor, stabilizer, a sweetener, oleic acid, oleic acid salt, and oleic acid ester;
    wherein said acid extraction extract is prepared by extracting *Rubus suavissimus* S. Lee (Rosaceae) in an aqueous acid solution at pH 4.0 or less;
    wherein said acid extraction extract is included in an amount ranging from 0.01% to 0.1% by weight of the fermented milk food as calculated in terms of an extract adjusted to 10 degrees Brix (sugar content); and
    wherein said extract is present in an amount sufficient to increase the proliferation of the *Lactobacillus casei* during fermentation of the fermented milk food compared to the proliferation of *Lactobacillus casei* in an otherwise identical fermented milk food fermented without the extract.

* * * * *